(12) United States Patent
Rathore et al.

(10) Patent No.: US 7,989,586 B2
(45) Date of Patent: Aug. 2, 2011

(54) MULTIBLOCK COPOLYMERS HAVING IMPROVED MECHANICAL PROPERTIES

(75) Inventors: Osman Rathore, Jacksonville, FL (US); Dotsevi Y. Sogah, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 46 days.

(21) Appl. No.: 12/197,646

(22) Filed: Aug. 25, 2008

(65) Prior Publication Data

US 2009/0143567 A1 Jun. 4, 2009

Related U.S. Application Data

(60) Division of application No. 11/113,494, filed on Apr. 25, 2005, now Pat. No. 7,417,112, which is a continuation of application No. 10/436,611, filed on May 13, 2003, now abandoned.

(60) Provisional application No. 60/380,502, filed on May 13, 2002.

(51) Int. Cl.
*C07K 7/00* (2006.01)
*C07K 7/02* (2006.01)

(52) U.S. Cl. .................................. 530/323; 530/329

(58) Field of Classification Search .................. None
See application file for complete search history.

(56) References Cited

U.S. PATENT DOCUMENTS

| 5,656,611 A | 8/1997 | Kabanov et al. |
| 6,221,959 B1 | 4/2001 | Kabanov et al. |

OTHER PUBLICATIONS

Rathore & Sogah "Nanostructure Formation through b-Sheet Self-Assembly in Silk-Based Materials," Macromolecules 2001, 34, 1477-1486.*
Hinman, M.B., Jones, et al., "Synthetic Spider Silk: A Modular Fiber," *Tibtech*, 18:384-5 (2000).
Liivak, O., Blye, et al., "A Microfabricated Wet-Spinning Apparatus to Spin Fibers of Silk Proteins: Structure—Property Correlations," *Macromolecules*, 31(9):2947-51 (1998).
Minoura, N., et al., "Physico-chemical Properties of Silk Fibroin Membrane as a Biomaterial," *Biomaterials*, 11:430-4 (1990).
Rathore, O., et al., "Self-Assembly of β-Sheets into Nanostructures by Poly(alanine) Segments Incorporated in Multiblock Copolymers Inspired by Spider Silk," *J Am Chem So.*, 123:5231-9 (2001).
Seidel, A., Liivak., et al. "Regenerated Spider Silk: Processing, Properties and Structure," *Macromolecules*, 33:775-80 (2000).
Winningham, M.J., et al., "A Modular Approach to Polymer Architecture Control via Catenation of Prefabricated Biomolecular Segments: Polymers Containing Parallel β-Sheets Templated by a Phenoxathiin-Based Reverse Turn Mimic," *Macromolecules*, 30(4):862-76 (1997).
U.S. Patent and Trademark Office Interview Summary dated Apr. 21, 2008 from corresponding U.S. Appl. No. 11/113,494, filed Mar. 25, 2005, Issued as U.S. Patent No. 7,417,112 on Aug. 26, 2008.
U.S. Patent and Trademark Office Advisory Action dated Mar. 26, 2008 from corresponding U.S. Appl. No. 11/113,494, filed Mar. 25, 2005, Issued as U.S. Patent No. 7,417,112 on Aug. 26, 2008.
Response to Final Office Action dated Feb. 13, 2008 under 37 C.F.R. 1.116, from corresponding U.S. Appl. No. 11/113,494, filed Mar. 25, 2005, Issued as U.S. Patent No. 7,417,112 on Aug. 26, 2008.
U.S. Patent and Trademark Office Final Office Action dated Feb. 13, 2008 from corresponding U.S. Appl. No. 11/113,494, filed Mar. 25, 2005, Issued as U.S. Patent No. 7,417,112 on Aug. 26, 2008.
Reply to Office Action dated Sep. 12, 2007 from corresponding U.S. Appl. No. 11/113,494, filed Mar. 25, 2005, Issued as U.S. Patent No. 7,417,112 on Aug. 26, 2008.
U.S. Patent and Trademark Office Non Final Office Action dated Sep. 12, 2007 from corresponding U.S. Appl. No. 11/113,494, filed Mar. 25, 2005, Issued as U.S. Patent No. 7,417,112 on Aug. 26, 2008.
Reply to Restriction Requirement dated Jul. 16, 2007 from corresponding U.S. Appl. No. 11/113,494, filed Mar. 25, 2005, Issued as U.S. Patent No. 7,417,112 on Aug. 26, 2008.
U.S. Patent and Trademark Office Restriction Requirement dated Jun. 22, 2007 from corresponding U.S. Appl. No. 11/113,494, filed Mar. 25, 2005, Issued as U.S. Patent No. 7,417,112 on Aug. 26, 2008.
U.S. Patent and Trademark Office Final Office Action dated Dec. 23, 2004 from corresponding U.S. Appl. No. 10/436,611, filed May 13, 2003, Abandoned.
Response A in reply to Office Action dated May 28, 2004 from corresponding U.S. Appl. No. 10/436,611, filed May 13, 2003, Abandoned.
U. S Patent and Trademark Office Non Final Office Action dated May 28, 2004 from corresponding U.S. Appl. No. 10/436,611, filed May 13, 2003, Abandoned.
Response to Restriction Requirement, on Apr. 23, 2004 from corresponding U.S. Appl. No. 10/436,611, filed May 13, 2003, Abandoned.
U.S. Patent and Trademark Office Restriction Requirement dated Mar. 24, 2004 from corresponding U.S. Appl. No. 10/436,611, filed May 13, 2003, Abandoned. Rathore et al., A novel silk-based segmented block copolymer containing GlyAlaGlyAla beta sheets templated by phenoxathiin, 2000, Journal of Polymer science Part A: Polymer chemistry, vol. 38, 352-366.

* cited by examiner

*Primary Examiner* — Christina Bradley
(74) *Attorney, Agent, or Firm* — Burns & Levinson, LLP; Jacob N. Erlich, Esq.; Janine M. Susan

(57) ABSTRACT

Replacement of the amorphous peptide domain of a structural biopolymer, such as silk from silkworms or spiders, with a nonpeptide segment while maintaining the β-sheet forming crystalline segments provides synthetic multiblock copolymers having solid-state structures and mechanical properties similar to the naturally occurring structural biopolymer is described herein. Such synthetic multiblock copolymers may be produced as films or fibers.

2 Claims, 13 Drawing Sheets

P2, x ~4, n ~13 (SEQ ID NO:1)

P3, x ~6, n ~13 (SEQ ID NO: 3)

P1, n ~13 (SEQ ID NO:13)

(SEQ ID NOS: 32-40)  (SEQ ID NOS: 42-50)

US 7,989,586 B2

MULTIBLOCK COPOLYMERS HAVING IMPROVED MECHANICAL PROPERTIES

RELATED APPLICATIONS

This application is a divisional of U.S. Ser. No. 11/113,494, filed Apr. 25, 2005 now U.S. Pat. No. 7,417,112, which is a continuation of U.S. Ser. No. 10/436,611, filed May 13, 2003 now abandoned, which claims priority to and the benefit of U.S. Ser. No. 60/380,502, filed May 13, 2002, all of which are incorporated herein by reference in their entirety.

GOVERNMENT SUPPORT

This invention was supported in part by National Science Foundation grants DMR-9632275 and DMR-0079992. Therefore, the United States government has certain rights to this invention.

FIELD OF THE INVENTION

This invention relates generally to novel mutiblock copolymers and, more particularly to multiblock copolymers having β-sheet forming cystalline segments and nonpeptide segments incorporated therein and a method of producing such multiblock copolymers.

BACKGROUND OF THE INVENTION

Nature maintains remarkable control over the nanostructure of structural biopolymers, such as silks, elastic, collagen, keratin, and amelogenin, through the manipulation of primary polypeptide sequences to achieve desired functionality. Not only do such natural biopolymers precisely fit their purpose, but in many cases, these materials have a multitude of attributes, each of which is optimized. For example, spider silk is a water-insoluble fiber with outstanding strength and toughness, properties usually considered to be mutually exclusive, that is spun at close to ambient conditions using water as the solvent. Moreover depending on the composition, this silk can be highly elastic or inelastic. These unique combinations of properties are inherently necessary to protect the web from bombardment with foreign objects and the impact energy generated by insects colliding and becoming ensnared in the web. Silkworm silk also has many of these highly desirable mechanical properties. All of these silks are very durable and resistant to degradation.

Applications for fibers or films having the attributes of structural biopolymers, such as spider or silkworm silk, include uses such as tissue-engineering scaffolds, cell-culture substrates, biocompatible coatings, sutures, membranes, grafts, and drag delivery systems among others. However, it is not cost-effective to attempt to harvest the naturally occurring silks for these purposes.

It is therefore an object of this invention to provide synthetic polymers having properties comparable or superior to naturally occurring structural biopolymers, such as silks.

It is another object of this invention to provide fibers and films having high strength and toughness comparable or superior to naturally occurring structural biopolymers, such as silks, that are capable of large-scale production.

SUMMARY OF THE INVENTION

Hybrid multiblock copolymers containing amino acid sequences derived from proteins found in structural biopolymers and synthetic nonpeptide chains are disclosed. Certain segments of the structure of naturally occurring structural biopolymers are replaced with a selected non-native segment while retaining the β-sheet forming segments of the structural biopolymer in order to produce a synthetic polymer with similar or improved properties and function to the naturally occurring biopolymer. Replacement of the amorphous peptide domain of a spider or silkworm silk, for example, with a synthetic nonpeptide segment, such as PEG (polyethylene glycol), produces polymers having similar solid-state structures and mechanical properties to spider silk. By maintaining the crystalline segment, the tendency to form β-sheets and the facility with which the β-sheets aggregate are retained in the synthetic copolymers and the desired mechanical properties are achieved.

The multiblock copolymers comprise the following structure:

-[peptide-linker$_1$-peptide]-linker$_2$-[peptide-linker$_3$-peptide]

wherein the peptide blocks are derived from peptide sequences found in the crystalline domains of *N. clavipes* or *B. mori* silks, wherein said linkers 1, 2, and 3 have the general formula $(A_xB)_n$ wherein A is either CRR' or SiRR', if A is CRR' then x is an integer from 1 to 4 and R and R' are independently chosen from H, methyl, ehtyl,propyl, and B is a heteroatom such as O, N, or S, wherein if B is N then the substituents on B are chosen from H, methyl, ethyl, or propyl groups, if A is $CH_2$ or $(CH_2)_2$ then n<20, if A is $(CH_2)_3$ or $(CH_2)_4$ then n is greater than or equal to 3; or if A is SiRR' then x is 1 and R and R' are independently chosen from methyl, ethyl, and vinyl.

The objects set forth above as well as further objects and advantages of the present invention are achieved by the invention described hereinbelow.

DETAILED DESCRIPTION

Structural biopolymers, such as silks, elastic, collagen, keratin, and amelogenins, contain highly repetitive sequences that can be correlated to various peptide blocks and β-sheet forming hard segments. Synthetic multiblock copolymers having properties similar to naturally occurring structural biopolymers are produced by replacing the peptide segments with functionally similar, but simpler block sequence and alternating such block sequences with the β-sheet forming segments or close approximations thereof to produce the self-assembly characteristics of the naturally occurring biopolymer and the associated properties.

Naturally occurring silks consist of β-sheet crystalline segments (e.g., (GlyAlaGlyAlaGlySer)$_m$, SEQ ID NOs: 22-30 for silk from the silkworm, *Bombyx mori* or (Ala)$_m$, SEQ ID NOs: 1-12 for silk from the spider, *Nephila clavipes*) that alternate with amorphous segments composed of amino acids some of which have bulky side groups. More particularly, these segmented multiblock copolymers contain alternating poly(alanine) segments and/or blocks of other amino acids such as (GlyAlaGlyAla)$_m$, SEQ ID NOs: 13-21, and/or (GlyAlaGlyAlaGlySer)$_m$, SEQ ID NOs: 22-30. For copolymers containing poly(alanine) segments, the number of Ala residues per segment is 2 to 15, with the average most preferably being 4 to 9, which is in the range where the poly(alanine) forms β-sheets rather than helices.

TABLE 1

Permutations of variable Ala residues from 4 to 15 with their respective SEQ ID NOS.

| | |
|---|---|
| (Ala)$_n$, where n = 4 | SEQ ID NO. 1 |
| (Ala)$_n$, where n = 5 | SEQ ID NO. 2 |
| (Ala)$_n$, where n = 6 | SEQ ID NO. 3 |
| (Ala)$_n$, where n = 7 | SEQ ID NO. 4 |
| (Ala)$_n$, where n = 8 | SEQ ID NO. 5 |
| (Ala)$_n$, where n = 9 | SEQ ID NO. 6 |
| (Ala)$_n$, where n = 10 | SEQ ID NO. 7 |
| (Ala)$_n$, where n = 11 | SEQ ID NO. 8 |
| (Ala)$_n$, where n = 12 | SEQ ID NO. 9 |
| (Ala)$_n$, where n = 13 | SEQ ID NO. 10 |
| (Ala)$_n$, where n = 14 | SEQ ID NO. 11 |
| (Ala)$_n$, where n = 15 | SEQ ID NO. 12 |

For copolymers containing (GlyAlaGlyAla)$_m$, SEQ ID NOs: 13-21, and/or (GlyAlaGlyAlaGlySer)$_m$, SEQ ID NOs: 22-30, m can be varied from 1 to 9. The multiblock copolymers of the present invention replace the segments in the amorphous domain of silk and other structural biopolymers with synthetic nonpeptide segments while retaining the poly(alanine) segments.

TABLE 2

Permutations of variable (GlyAlaGlyAla)$_m$, SEQ ID NOs: 13-21, and (GlyAlaGlyAlaGlySer)$_m$, SEQ ID NOs: 22-30, sequences where m ranges from 1 to 9, together with their respective SEQ ID NO.

| (GlyAlaGlyAla)$_n$ | SEQ ID NO. | (GlyAlaGlyAlaGlySer)$_n$ | SEQ ID NO. |
|---|---|---|---|
| n = 1 | 13 | n = 1 | 22 |
| n = 2 | 14 | n = 2 | 23 |
| n = 3 | 15 | n = 3 | 24 |
| n = 4 | 16 | n = 4 | 25 |
| n = 5 | 17 | n = 5 | 26 |
| n = 6 | 18 | n = 6 | 27 |
| n = 7 | 19 | n = 7 | 28 |
| n = 8 | 20 | n = 8 | 29 |
| n = 9 | 21 | n = 9 | 30 |

Figure 1A:
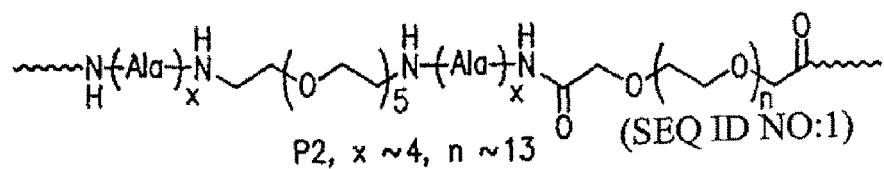
FIG. 1A shows the generic structure of a multiblock copolymer of the present invention, referred to herein as P2.
Figure 1B:
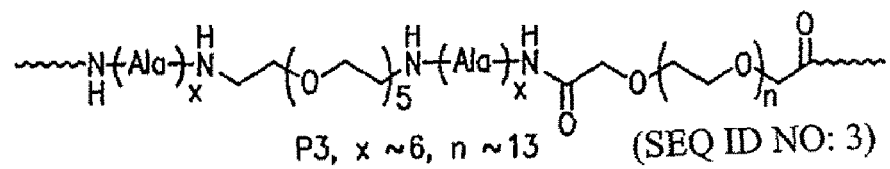
FIG. 1B shows the generic structure of another multiblock copolymer of the present invention, referred to herein as P3.

As shown in FIGS. 1A and 1B, in the multiblock copolymers P2 and P3 which are based on the structure of *N. clavipes* silk, the poly(alanine) blocks have variable chain lengths and can be synthesized via standard polymerization techniques known in the art, such as anionic ring-opening polymerization of the N-carboxyanhydride (NCA) derivative of the amino acid.

Figure 2A:
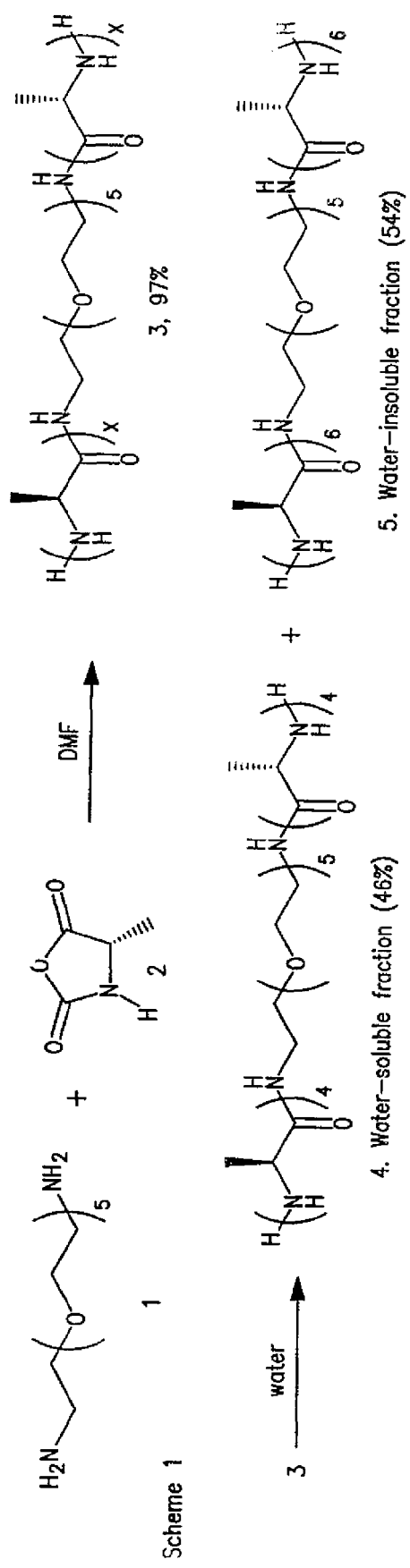
FIG. 2A shows the anionic ring polymerization of Ala-NCA (Alanine N-carboxyanhydride), referred to herein as Scheme 1.

The average number of Ala residues in *N. clavipes* silk (4 to 9), SEQ ID NOs: 1-6, are accessible via anionic ring-opening polymerization of the NCA derivative of the amino acid. The degree of polymerization (DP) can be readily controlled by the molar ratio of the NCA to the initiator, which is typically a Lewis base. Referring to FIG. 2A, anionic ring-opening polymerization of Ala-NCA (2) using a,w-diamino-PEG (1) as the initiator gave the triblock material poly(alanine-b-oxyethylene-b-alanine). The poly(alanine-b-oxyethylene-b-alanine) is fractionated into water-soluble (4) and water-insoluble (5) components. End-group titration of 4 and 5 gave number average molecular weights ($M_n$'s) as 823 and 1097, respectively. These correspond, respectively, to approximately 8 and 12 Ala residues SEQ ID NOs: 5 and 9, respectively), which are equivalent to an average DP of 4 and 6 for each poly(alanine) block.

Figure 2B:
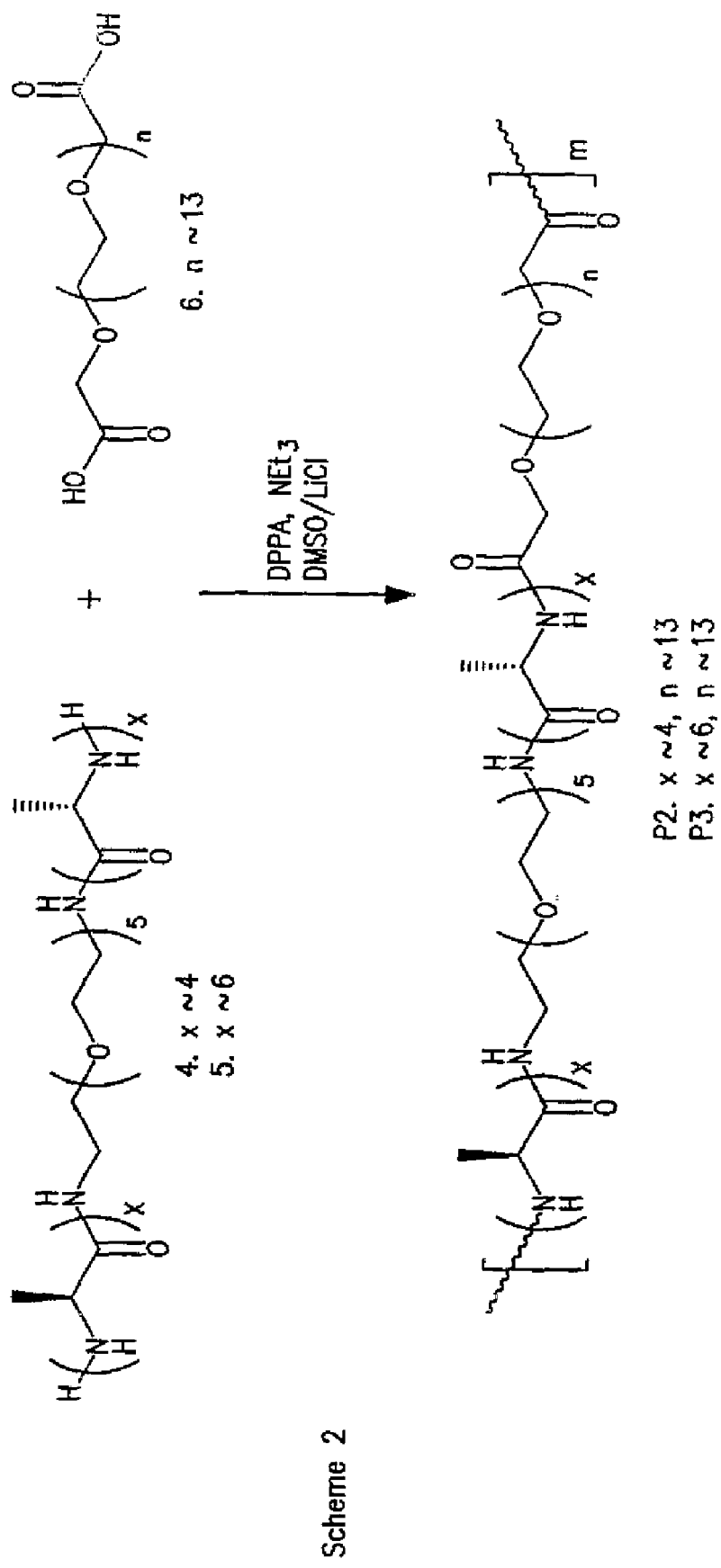
FIG. 2B shows the step growth polymerization of P2 and P3.

Now turning to FIG. 2B, polymers P2 and P3 are prepared by step-growth polymerization of 4 and 5, respectively, with the commercially available poly(ethylene glycol) bis(carboxymethyl)ether (6) as the chain extender in LiCl/DMSO (LiCl lithium chloride DMSO=dimethyl sulfoxide) and in the presence of DPPA/Et$_3$N (DPPA=diphenylphosphorylazide; Et$_3$N=triethylamine.

Preferably, PEG is utilized as the non-native equivalence of the amorphous polypeptide domain due to its ready availability, ease of synthesis, well-established properties, water-solubility, biocompatibility, and controllable amorphous and crystalline character, but those skilled in the art will recognize that other nonpeptides having the desired characteristics may be utilized. The lengths of the PEG segments are preferably kept short to prevent unwanted crystallization of the PEG block and maintain the amorphous domain.

The polymers P2 and P3 are relatively insoluble even in a LiCl/DMSO mixture; therefore inherent viscosity ($\eta_{inh}$) measurements in dichloroacetic acid were used to obtain information about their molecular weights. The $\eta_{inh}$ of 0.42 dL·g$^{-1}$ for P2 and 0.31 dL·g$^{-1}$ for P3 correspond to weight average molecular weights ($M_w$'s) of ca. 20000-25000 and ca. 15000-20000, respectively, based upon similar measurements reported earlier.

Figure 3A:
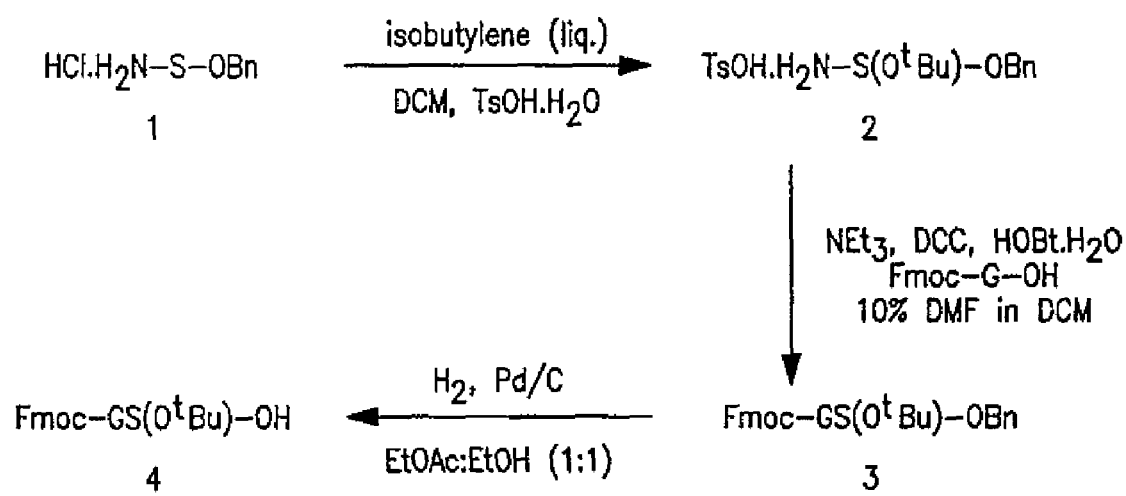
FIGS. 3A and 3B show a synthesis scheme for P1.
Figure 3B:
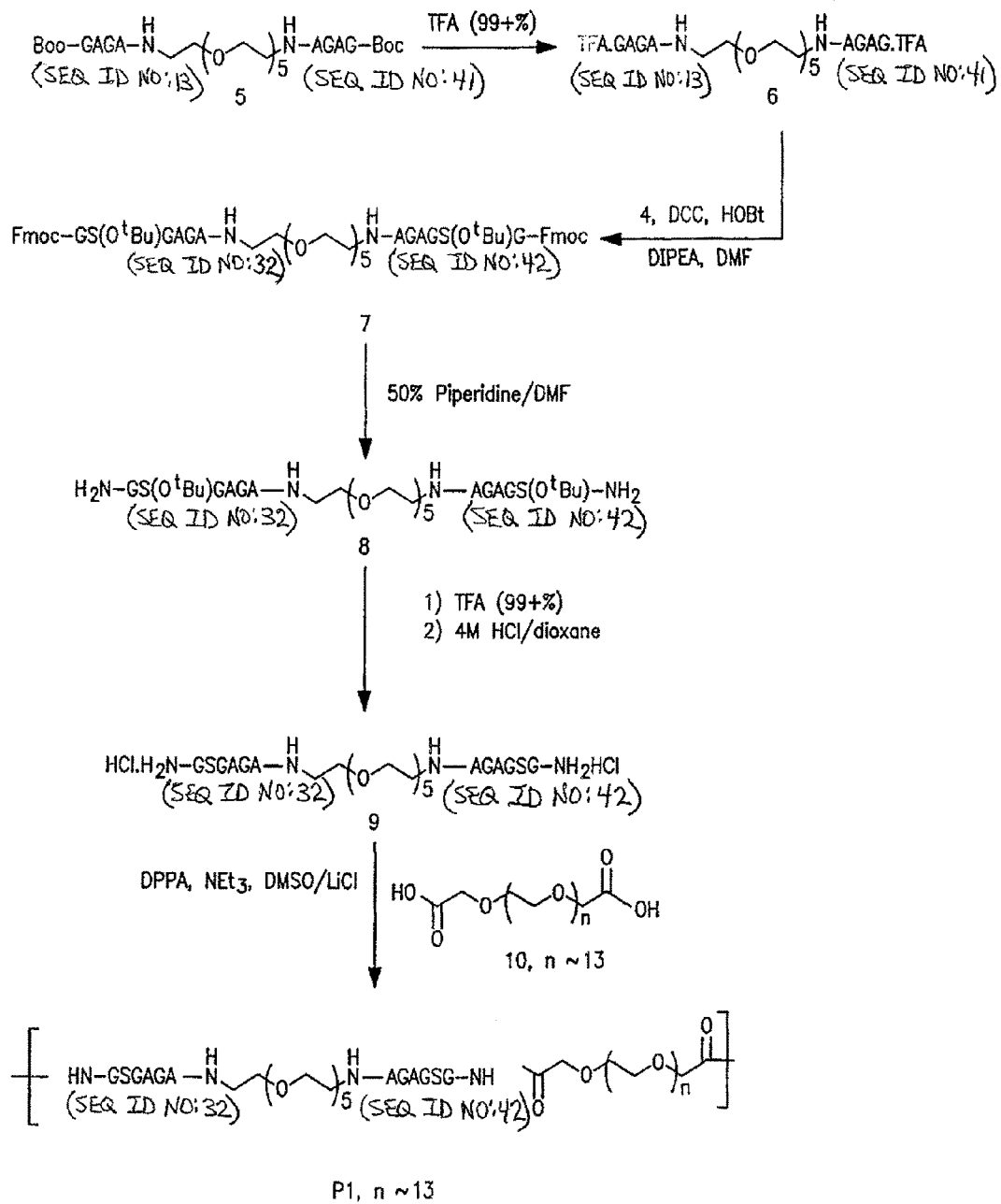

The *B. mori* silk-inspired polymer P1 shown in FIG. 3B was prepared as shown in FIGS. 3A and 3B. Monomer (7) for Pt is obtained by coupling the GlyAlaGlyAla (SEQ ID NO.

31) containing compound (5) to Fmoc-GlySer(O$^t$Bu)-OH (Fmoc=9-Fluorenylmethoxy-carbonyl) using DCC/HOBt (DCC=dicyclohexyl carbodiimide; HOBt=1-hydroxy-benzotriazole). Standard deprotection of the Fmoc-group with piperidine/DMF (DMF=dimethylformamide), and of the t-butyl group with TEA (TFA=trifluoroacetic acid), followed by treatment with HCl/dioxane (HCl=hydrogen chloride), yielded the hexa(ethylene glycol)-based peptidic diamine salt (9). The preparation of P1 was effected by catenation of (9) with the commercially available poly(ethylene glycol) bis (carboxymethyl)ether (10) in solution (DMSO/DPPA/Et$_3$N). Viscosity measurements in dichloroacetic acid gave inherent viscosity of 0.68 dL.g$^{-1}$ for P1. This corresponds to an estimated weight-average molecular weight (Mw) of about 30,000 to about 35,000.

TABLE 3

Variations in peptide sequence for P1, where n ranges from 1 to 9.

| (GlySerGlyAlaGlyAla)$_n$ | SEQ ID NO. |
|---|---|
| n = 1 | 32 |
| n = 2 | 33 |
| n = 3 | 34 |
| n = 4 | 35 |
| n = 5 | 36 |
| n = 6 | 37 |
| n = 7 | 38 |
| n = 8 | 39 |
| n = 9 | 40 |

TABLE 3A

| (AlaGlyAlaGlySerGly)$_m$ | SEQ ID NO |
|---|---|
| m = 1 | 42 |
| m = 2 | 43 |
| m = 3 | 44 |
| m = 4 | 45 |
| m = 5 | 46 |
| m = 6 | 47 |
| m = 7 | 48 |
| m = 8 | 49 |
| m = 9 | 50 |

The extent of self-assembly into nanostructures in silk-inspired materials has been shown to correlate with their β-sheet contents. Solid-state $^{13}$C NMR and solid-state FTIR were utilized to demonstrate the formation of β-sheets in the copolymers of the present invention. Solid-state FTIR spectroscopy also provides a means to distinguish between parallel and antiparallel β-sheets. The formation of antiparallel β-sheets was also confirmed by powder X-ray diffraction. The modulus and tensile strength of P2 and P3 were determined from stress-strain curves of their respective films and fibers to show the physical properties of the multiblock copolymers of the present invention.

Common reagents were purchased from Aldrich, Sigma or Acros and solvents from Fisher Scientific or Mallinckrodt. CH$_2$Cl$_2$ (methylene chloride) was distilled from CaH$_2$ (calcium hydride) and stored over 3 Å molecular sieves. PCl$_3$ (phosphorous trichloride) was refluxed and distilled prior to use. THF and toluene were distilled from purple Na/benzophenone solutions. DMSO was distilled from CaH$_2$ onto 4 Å molecular sieves. Glassware was dried in an oven and cooled under nitrogen where appropriate. Synthesis of 3,6,9,12,15-pentaoxaheptadecane-1,17-diamone (1) and the N-carboxyanhydride derivative of Ala (2) were performed in accordance with methods known in the art. The 3,6,9,12,15-pentaoxaheptadecane-1,17-diamone was further purified using Kugelrohr distillation. Instead of washing with CCl$_4$ (carbon tetrachloride), the crude Ala-NCA (2) was recrystallized twice from THF (tetrahydrofuran)/toluene. Poly(ethylene glycol) bis(carboxymethyl)ether (6, M$_n$~600 was purchased from Aldrich and used without purification.

P2 and P3 films were obtained by casting onto glass slides from 50% (w/v) HFIP (hexafluoroisopropanol) solutions using a micron film applicator from CARDCO. The glass slides were sprayed prior to use with Fluoroglide anti-stick agent to facilitate lift-off. The films were dried at 70-75° C. overnight in vacuo prior to testing. Continuous fibers were spun from P2 (10-15% w/v HFIP solution) and from (5% w/v HFIP solution) by extruding the spinning dope contained in a 100 μL LuerLok syringe equipped with a needle having an internal diameter of 350 μm and a length of 8 mm. The coagulant used was methanol-acetone (1:1), and the extruded filaments were allowed to cure for 1 h in the bath prior to removal by reeling. The fibers were dried at 70-80° C. overnight in vacuo prior to testing.

The 3,6,9,12,15-pentaoxaheptadecane-1,17-diamidolbis [poly(alanine)] was synthesized by adding Ala-NCA (2, 3.23 g, 28.06 mmol) to a 250-mL round-bottom flask equipped with a stirring bar. The flask was sealed with a rubber septum and 40 mL of DMF was introduced via cannulation. The mixture was stirred until the solids dissolved after which a solution of 1 (0.655 g, 2.34 mmol) in 5 mL of DMF was added via a syringe under nitrogen. The mixture was allowed to stir at room temperature under nitrogen atmosphere for 1 day. The reaction mixture was precipitated into 400 mL of diethyl ether and filtered. The solids thus obtained were washed with absolute ethanol (3×30 mL) and acetone (3×30 mL). The resulting white powder was dried in vacuo to yield 3 (2.57 g. 97%). The product was fractionated by treatment with 75 mL of water. The water-insoluble material was filtered and dried in vacuo to yield 5 (1.3 g): mp 191.5-195.1° C. dec. $^1$H NMR (300 MHz, ppm, TFA-d): δ 4.70 (m, Ala-αH), 4.51 (m, Ala-αH), 3.93 (m, —OCH$_2$CH$_2$— and OCH$_2$CH$_2$NH—), 3.70 (m, —OCH$_2$CH$_2$NH—), 1.40-1.81 (overlapped d, Ala-βH). End-groups (by aqueous titration): 1.823 mmol/g. M$_n$=1097 (by end-group analysis). ESIMS (electrospray ionization mass spectroscopy) (m/z, relative intensity): 778.4, 30%; 849.4, 56%; 920.8, 95%; 991.8, 100%; 1062.6, 58%; 1133.2, 24%; 1205.2, 14%. Elemental analysis: C, 49.32; H, 8.02; N, 16.72.

The filtrate was lyophilized to obtain 4 (1.1 g): mp 186.7° C. dec. $^1$H NMR (300 MHz, ppm, D$_2$O): δ 4.25 (m, Ala-αH), 3.86 (m, Ala-αH), 3.66 (m, —OCH$_2$CH$_2$—), 3.59 (collapsed dt, OCH$_2$CH$_2$NH—), 3.37 (m, —OCH$_2$CH$_2$NH—), 1.12-1.49 (overlapped d, Ala-βH). End-groups (by aqueous titration): 2.431 mmol/g. M$_n$=823 (by end-group analysis). ESIMS (m/z, relative intensity): 565.9, 5%; 636.5, 20%; 707.5, 47%; 778.6, 100%; 849.7, 93%; 920.9, 43%; 991.7, 11%. Elemental analysis: C, 48.88; H, 7.75; N, 15.20.

Preparation of P2: To a 25 mL round-bottom flask equipped with a magnetic stirring bar and a gas-inlet adapter, 4 (0.500 g, 1.22 mmol —NH$_2$ groups), 6 (0.424 g, 1.22 mmol —COOH groups), and 10 mL of 2.5% LiCl in DMSO were added. The mixture was cooled to ~12-15° C. and NEt$_3$ (0.68 mL, 4.88 mmol) and DPPA (0.34 mL, 1.58 mmol) were added. The reaction was stirred rapidly at 12-15° C. for 10 min and then allowed to warm to room temperature. After 2 days the mixture was again cooled to ~12-15° C. and NEt$_3$ (0.40 mL, 2.87 mmol) and DPPA (o.34 mL, 1.58 mmol) were added. The reaction was stirred at room temperature for a further 2 days. The polymerization mixture was pipetted into 400 mL of EtOAc (ethyl acetate). The crude product was washed successively with diethyl ether (3×50 mL), MeOH (methanol) (3×50 mL), and diethyl ether (2×50 mL). The resulting off-white solid was dried in vacuo to yield P2 (672 mg, 75%). DSC: $T_{g1}$ −58° C., $T_{g2}$ −28° C. TGA: $T_{d.onset}$ 307° C. $\eta_{inh}$=0.417. IR (KBr, 4.0 cm$^{-1}$): 3488 (sh), 3277, 3075, 2915, 1736, 1699, 1682 (sh), 1678, 1668, 1652, 1630, 1610, 1537, 1451, 1400, 1358, 1292, 1247, 1100. Elemental analysis: C, 50.89; H, 7.66; N, 9.55; P, <0.05.

Preparation of P3: The procedure for P2 was followed using 5 (0.500 g, 0.912 mmol —NH$_2$ groups), 6 (0.318 g, 0.912 mmol —COOH groups), NEt$_3$ (0.38 mL+0.30 mL, 2.73 mmol+2.15 mmol), DPPA (0.26 mL+0.26 mL, 1.21 mmol+1.21 mmol), and 20 mL of 2.5% LiCl in DMSO to give P3 (611 mg, 68%) as an off-white solid. DSC: $T_{g1}$ −54° C., $T_{g2}$ −18° C. TGA: $T_{d.onset}$ 337° C. $\eta_{inh}$=0.305. IR (KBr, 4.0 cm$^{-1}$): 3486 (sh), 3276, 3077, 2917, 1723, 1700, 1685 (sh), 1679, 1668, 1659, 1628, 1611, 1531, 1450, 1398, 1370, 1299, 1238, 1102. Elemental analysis: C, 50.71; H, 7.67; N, 12.08; P, <0.05.

Solution $^1$H and $^{13}$C NMR spectra were recorded on an AF-300 spectrophotometer. Solid-state $^{13}$C NMR spectra were recorded on an AF-300 spectrophotometer. Solid-state $^{13}$C NMR CPMAS spectra were recorded at 75.22 MHz on a "home-built" instrument. FTIR spectra were recorded on a Perkin-Elmer 16PC FIR spectrometer. Solid-state FTIR samples were prepared as 0.3-0.5 wt % in KBr pellets, and the spectra were obtained with 50 scans at a resolution of 2.0 cm$^{-1}$ for 1750-1600 cm$^{-1}$, and at 4.0 cm$^{-1}$ from 4000 to 1000 cm$^{-1}$. Inherent viscosity measurements were done in DCA (dichloroacetic acid) solutions with a Cannon-Ubbelohde C1 C866 viscometer, which was placed in a water bath thermostated at 25±0.1° C. Solubility tests of the polymers were carried out at 1 mg/mL concentration.

Thermogravimetric analysis (TGA) and differential scanning calorimetry (DSC) were performed on a Seiko 5200 thermal analysis system with TGA/DTA 220 and DSC 220 C units under a positive flow of nitrogen at a heating rate of 20 and 10° C./min, respectively. Glass transition temperatures ($T_g$'s) and melt transitions ($T_m$'s) were recorded from the second heating cycle. Melting points were measured on an Electrothermal IA90 melting point apparatus and are uncorrected. Powder X-ray diffraction was performed on a θ-θ Scintag diffractometer with a Cu source (λ=1.5405 Å). X-ray diffraction data for fibers were obtained on a Bruker-Axs D8 system (λ=1.5405 Å) with a 2-D detector at 40 kV and 40 mA. All X-ray diffraction data were smoothed for presentation without generating artifacts. Tensile measurements were performed on films and fibers using an Intron tensile testing system (series 1122) at 21° C. and 65% relative humidity. The ends of the films and fibers were immobilized onto pieces of cardboard that were then clamped during measurements. AFM samples were prepared by spin-coating a 10% (w/v) HFIP solution of the polymer on silicon wafers at 4000 rpm and immediately drying the wafer at 115° C. for 1 min in vacuo. The samples were visualized on a Nanoscope III (Digital Instruments), using a 12 μm D scanner in air, in the tapping mode. The AFM was mounted on a homemade anti-vibration table and on a isolation chamber. AFM tips from Digital Instruments with force constants of 50 N/m (manufacturer's specifications) were employed. A resonant frequency of 30 kHz was used.

Figure 4:
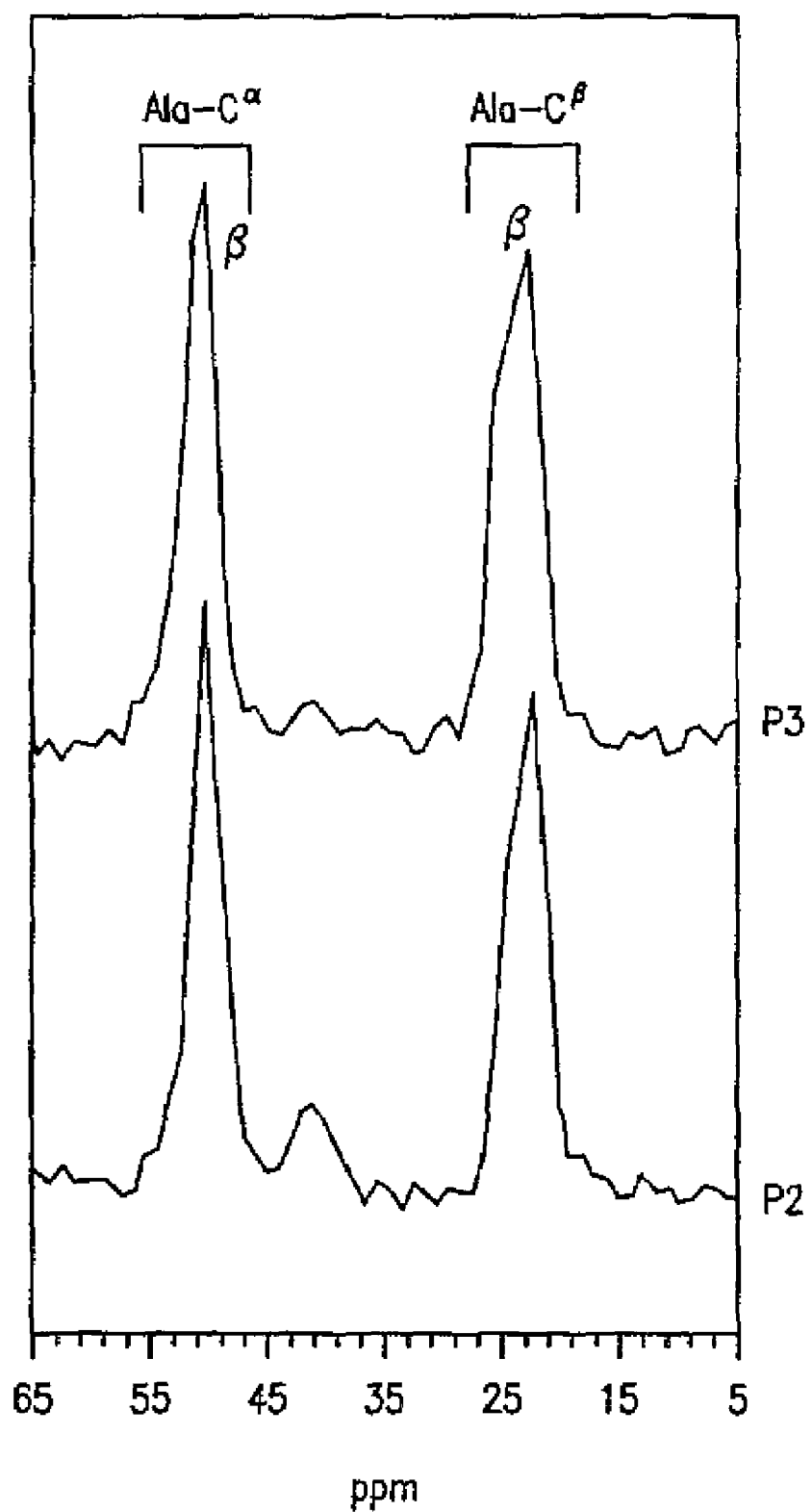
FIG. 4 shows the Ala-$C^\alpha$ and Ala-$C^\beta$ region in the solid-state 13C NMR (nuclear magnetic resonance) spectra of P2 and P3.

Referring now to FIG. 4, the solid-state $^{13}$C NMR spectra of P2 and P3 are depicted. The broad resonance at 22 ppm in the Ala-C$^\beta$ spectral region (14-24 ppm) of both P2 and P3 and the resonance at 49.5 ppm (AlaC$^\alpha$) are attributed to β-sheet aggregates. Furthermore, there is no noticeable shoulder either downfield (51-52 ppm) to the Ala-C$^\alpha$ peak or upfield (15-19 ppm) to Ala-C$^\beta$ peak in the spectra of both polymers, indicating that P2 and P3 did not form significant amounts of other major non-β-sheet conformations. The total β-sheet content in each polymer was estimated to be 95±5%, which is comparable to that found for the structurally similar P1 (90%) but higher than that reported for native *N. clavipes* silk (77%). The results are evidence that the predominant conformation of the poly(alanine) segments in both P2 and P3 is, indeed, a β-sheet.

Figure 5:
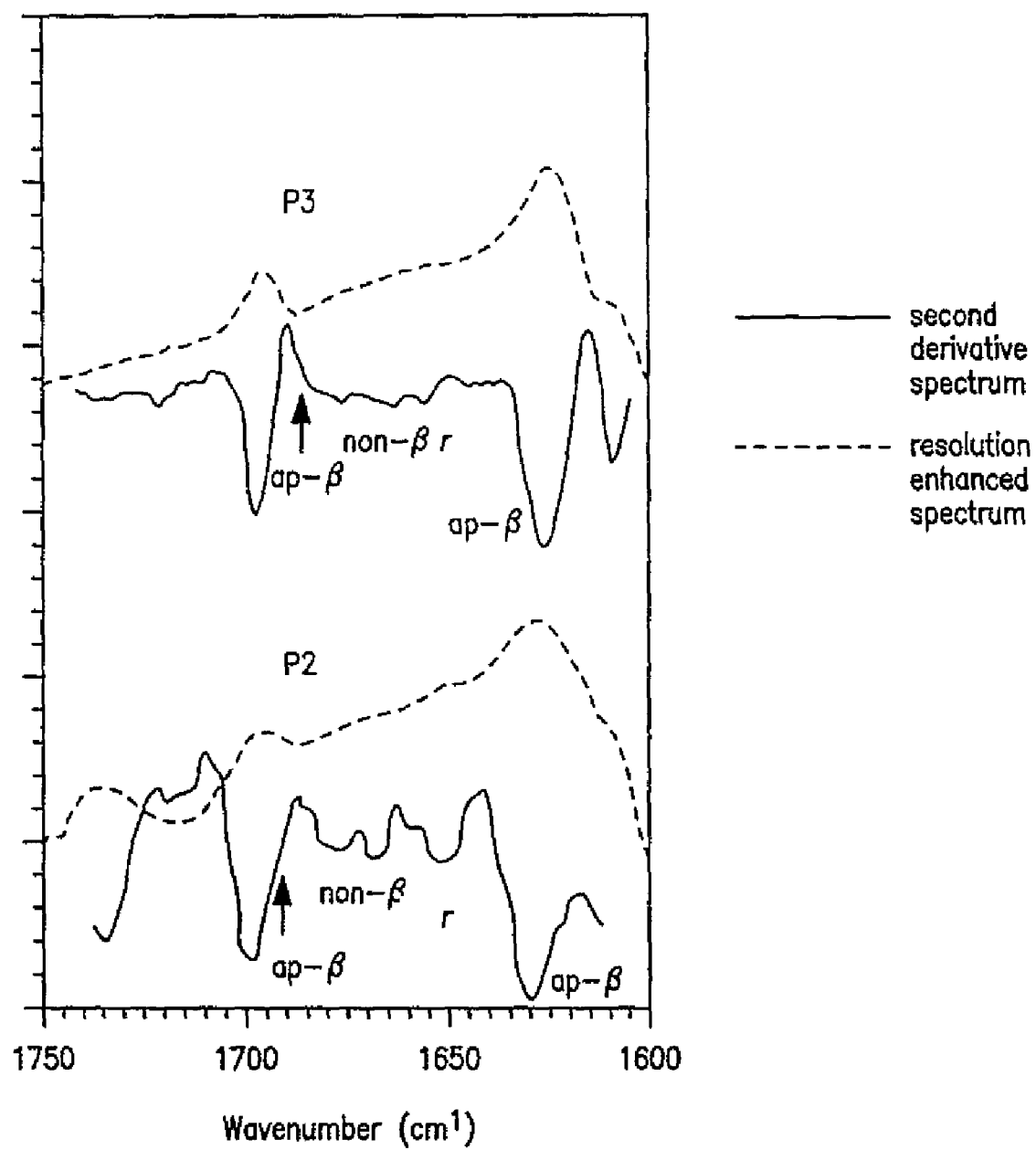
FIG. 5 shows solid-state FTIR Courier transform infrared) spectra of P2 and P3, specifically a resolution-enhanced spectrum of P2, a second derivative spectrum of P2, a resolution-enhanced spectrum of P3 and a second derivative spectrum of P3.

As shown in FIG. 5, the resolution enhanced and the second derivative solid-state FTIR spectrum of P2, the copolymer with shorter poly(alanine) segments, showed bands at 1630 and 1692 (shoulder) cm$^{-1}$. These bands have been shown to be diagnostic for antiparallel β-sheets. The FTIR spectrum also revealed bands due to random (r, 1655 cm$^{-1}$) and some non-β-sheet (non-β, 1663 and 1675 cm$^{-1}$) conformations; but these bands were considerably weaker than the bands attributed to the corresponding antiparallel β-sheets. Furthermore, there was no evidence for the presence of parallel β-sheets, which would have given rise to a band at approximately 1645 cm$^{-1}$ in addition to the 1630 cm$^{-1}$ band. The relatively large band at 1700 cm$^{-1}$ was from the amide carbonyl group of comonomer 6 fragments. The FTIR data clearly substantiate the deductions from the $^{13}$C NMR studies and establish that the β-sheets are indeed antiparallel.

Figure 6:
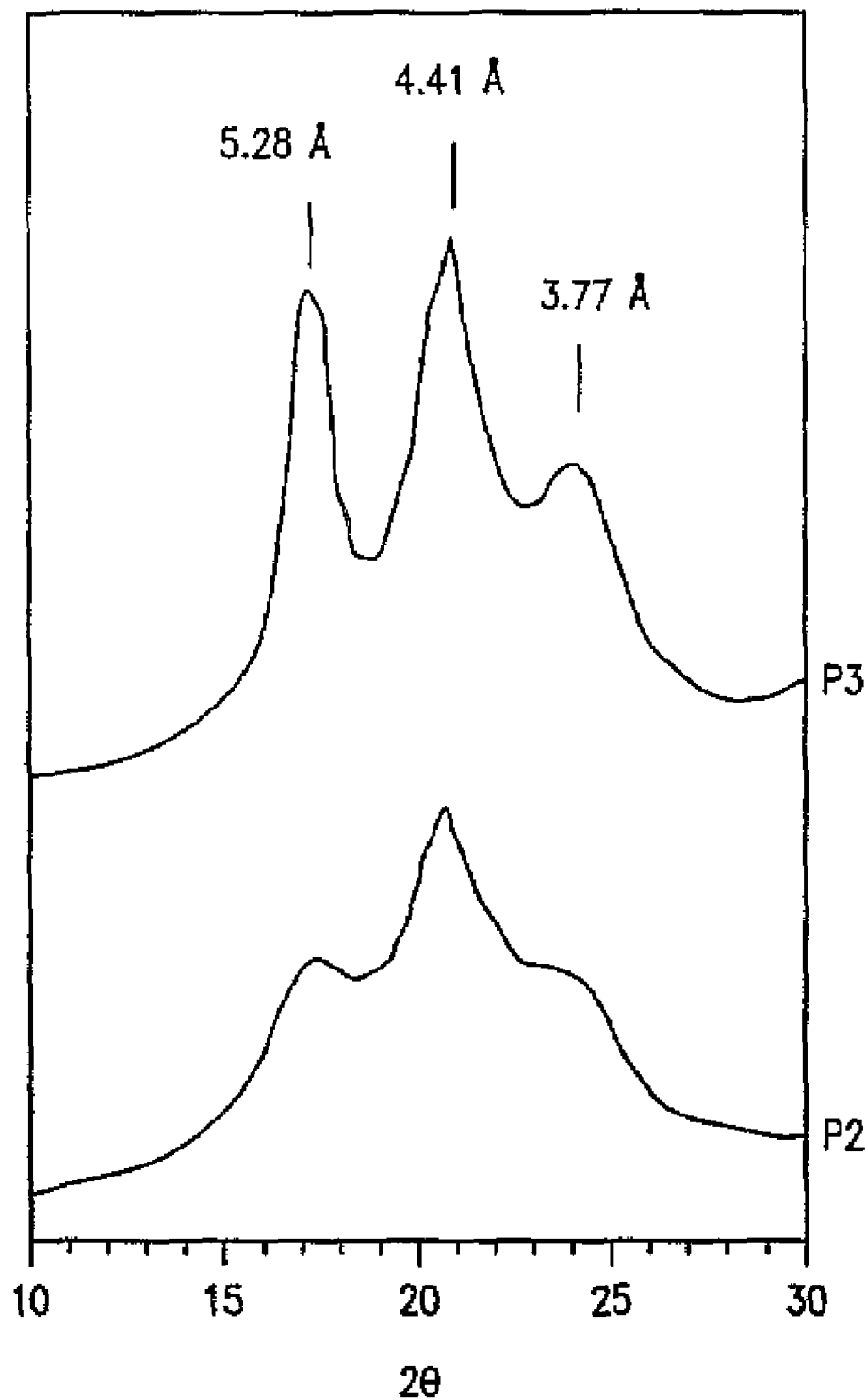
FIG. 6 shows a powder X-ray diffraction pattern of P2 and P3.
Figure 7A:
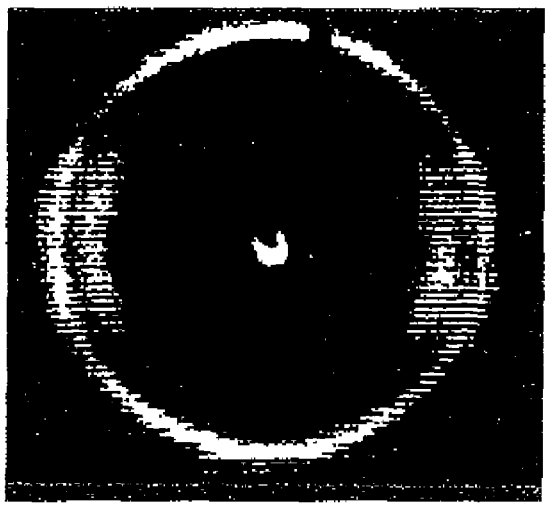
FIG. 7 shows WAXD (wide-angle x-ray diffraction) patterns of the as-spun P2 fiber bundle with the fiber axis vertical and the as-spun P3 fiber bundle with the fiber axis about 35° clockwise from vertical.
Figure 7B:
Figure 8:
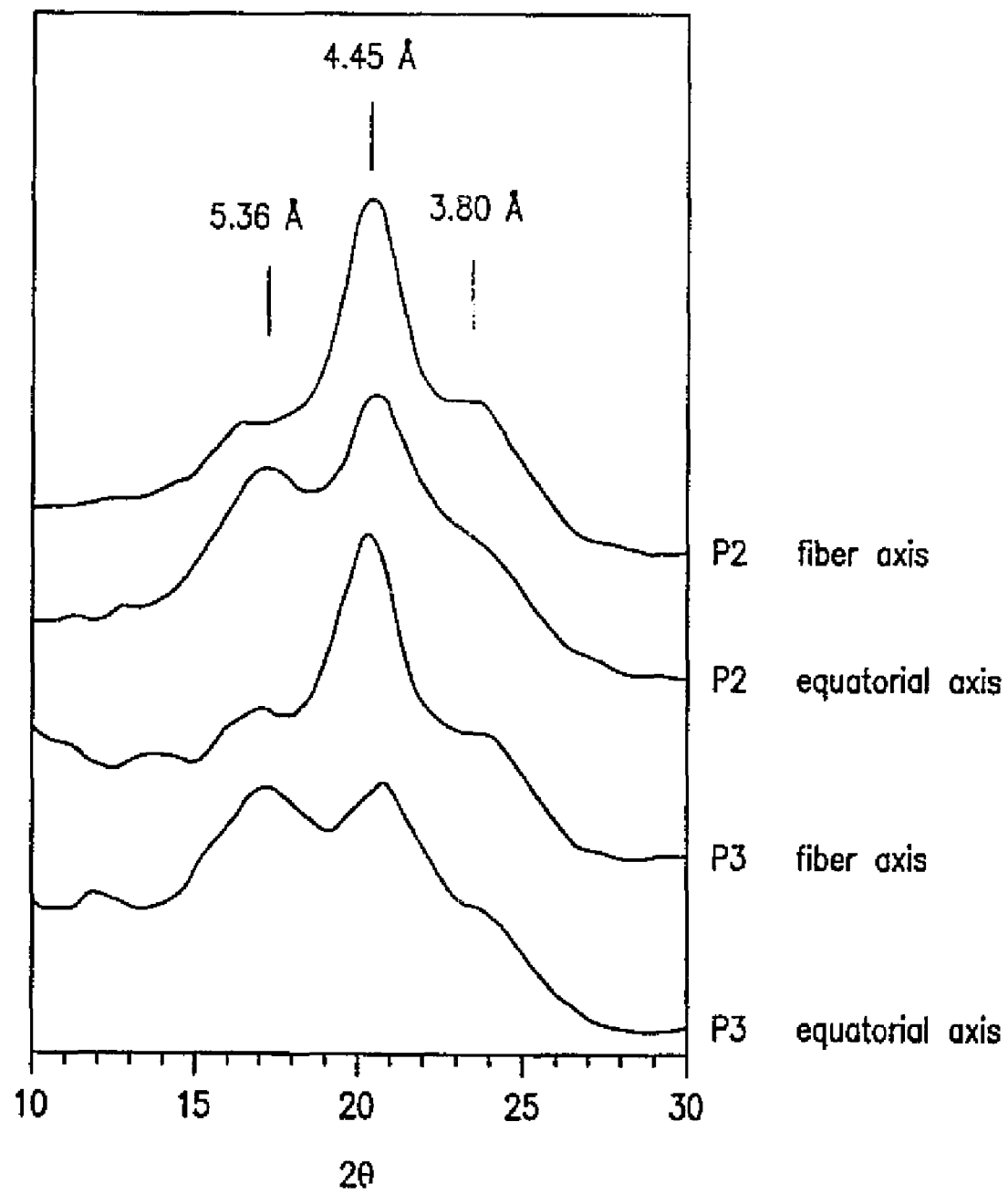
FIG. 8 shows radial intensity integration along the P2 fiber axis +/−45°, the P2 equatorial axis +/−45°, the P3 fiber axis +/−45°, and the P3 equatorial axis +/−45°.

In FIG. 6, the diffraction pattern of P2 showed peaks with d spacings of 5.28, 4.41, and 3.77 Å. These are similar to the antiparallel β-sheet d spacings for *N. clavipes* silk and those observed for a poly(alanine) β-sheet at 5.36 and 4.45 Å corresponding, respectively, to 020 and 100 reflections in an orthorhomic crystal with a=4.73 Å, b=10.54 Å, and c=6.89 Å. To determine if the chains were aligned in any manner, X-ray diffraction studies, as shown in FIG. 7, were carried out on fibers made from P2. The fiber X-ray diffraction of the P2 fibers gave arcs perpendicular the fiber axis rather than concentric circles, indicating the polymer chains were aligned relatively well parallel to the fiber axis. This was confirmed by integrating the relative intensities along the fiber and equatorial axes, as shown in FIG. 8. The d spacings of 4.45 and 5.36 Å were assigned respectively to the interchain spacing within a hydrogen-bonded sheet and the intersheet spacing in a poly(alanine) β-sheet. Hence, the solid-state FTIR and X-ray diffraction results demonstrate the poly(alanine) segments in P2 predominantly self-assemble into antiparallel β-sheet-containing nanostructures and that the crystalline structure is the same as that independently determined for an isolated poly(alanine).

Turning again to FIG. 5, the FTIR spectrum of the polymer containing the longer poly(alanine) segments (P3) is shown. The second derivative plot reveals that this polymer also formed predominantly antiparallel β-sheet stacks as evidenced by peaks at 1628 and 1690 (shoulder) cm$^{-1}$. The spectrum was almost completely devoid of any evidence for other non-β conformations, which is in complete agreement with the $^{13}$C NMR results. Further confirmation was obtained from powder X-ray diffraction analysis as shown in FIG. 8, which gave enhanced peak intensities at 5.28, 4.41, and 3.77 Å. As can be discerned from the spectrum, the peak at 5.28 Å, which denotes intersheet spacing in poly(alanine) β-sheets, is resolved better for P3 than for P2, which is consistent with its enhanced conformational purity.

Turning again to FIG. 7, X-ray diffraction analysis of P3 fibers is depicted. As was the case with P2, P3 polymer chains were fairly well aligned parallel to the fiber axis, which result in enhanced intensity of the peak at 5.36 Å integrated along the equatorial axis as shown in FIG. 8. These observations demonstrate that the β-sheets in both polymer chains could be aligned and oriented through fiber spinning, copolymers with higher β-sheet and lower random conformation contents exhibit higher structural order, and copolymers containing longer poly(alanine) segment have a higher propensity to self-assemble into ordered β-sheet domains.

Figure 9:
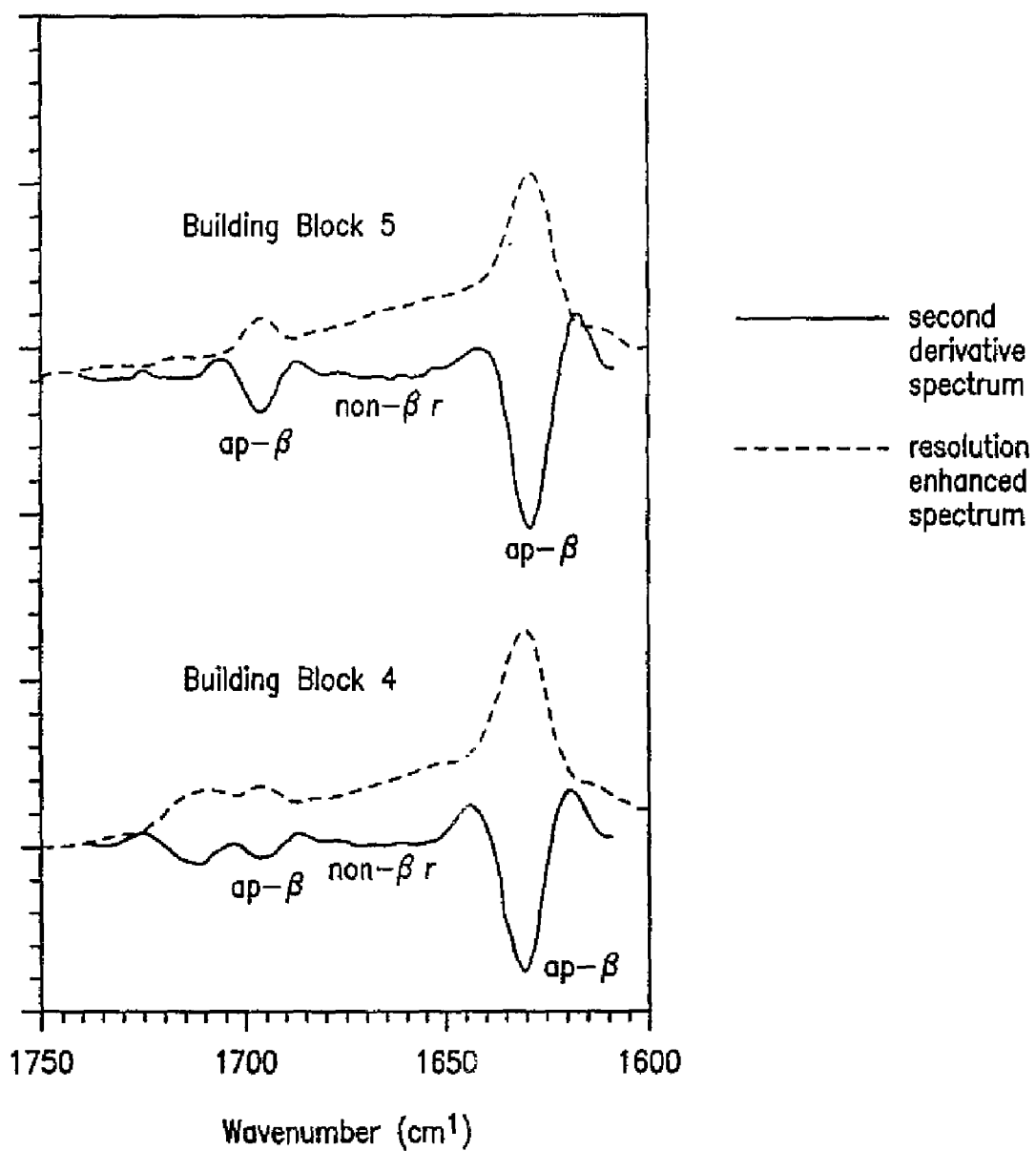
FIG. 9 shows solid-state FTIR spectra of components of the P2 and P3 polymers.

To determine the extent to which the structures of P2 and P3 are influenced by their respective building blocks, we examined the FITR spectra of 4 and 5, as depicted in FIG. 9. In FIG. 9, both resolution-enhanced spectrum and second-derivative spectrum are shown for 4 and 5. The solid-state structures of both 4 and 5 are also dominated by antiparallel β-sheets as evidenced by the diagnostic bands at 1630 and 1695 cm$^{-1}$ and the fact that the antiparallel β-bands are more intense than non-β bands. In addition, the antiparallel β-bands of 5 are resolved better and are relatively more intense than those for 4. These suggest that 5 contains higher antiparallel β-sheet fraction than 4. Hence, the observed relative propensity of P2 and P3 to form β-sheets tracks that of their respective building blocks.

Figure 10A:
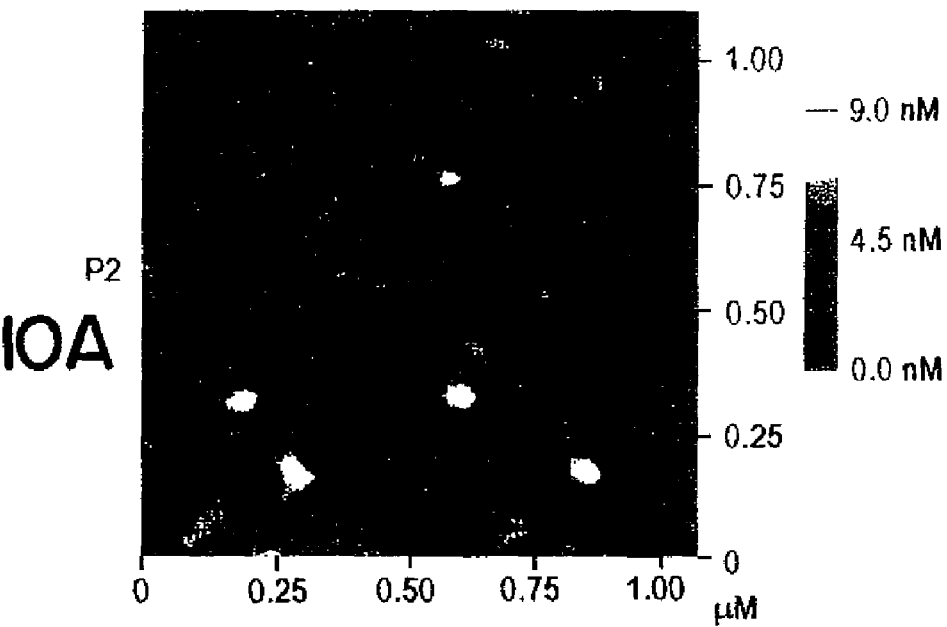
FIG. 10A shows a tapping mode AFM (atomic force microscopy) topological plot of P2 spin-coated on a silicon wafer.
Figure 10B:
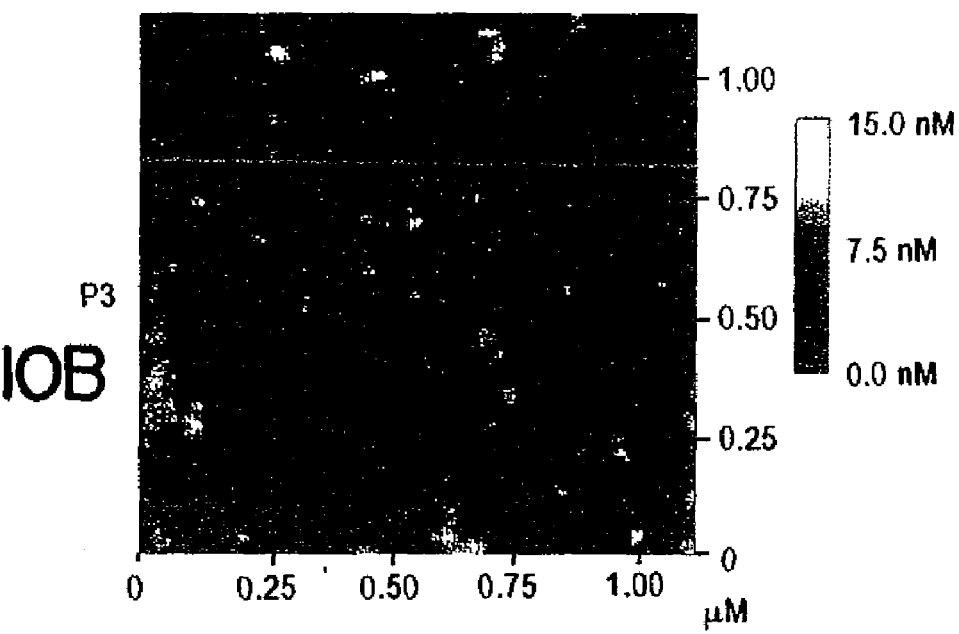
FIG. 10B shows a tapping mode AFM topological plot of P3 spin-coated on a silicon wafer.

The $^{13}$C NMR, FTIR, and X-ray studies show the presence of self-assembled antiparallel β-sheets in the copolymers of the present invention. Aggregation of the β-sheets into nanodomains lead to hard (semi)crystalline polypeptide domains that are phase-separated from the soft PEG domains. AFM, especially in the tapping mode, can distinguish between hard crystalline domains from soft amorphous ones. Hence, the morphology of P2 and P3 was studied using AFM in the tapping mode. FIGS. 10A and 10B show the AFM topographical plots of HFIP solution-cast films of P2 (top) and P3 (bottom) on silicon wafers. Under the conditions used, low regions are dark-colored while the higher regions are lighter colored; the lighter the color is, the harder and, hence, the higher is the domain. As can be seen in the AFM images, the hard semicrystalline poly-(alanine) domains are topographically higher (lightest in color) because they are stiffer than the soft PEG segments. FIGS. 10A and 10B reveal a microphase-separated morphology containing polypeptide rich and polyether-rich phases. In addition, larger domains (c. 100-200 nm) are seen superimposed on the normal microphase-separated morphology with the polyether phase dispersed between them.

Table 3B depicts synthesis and properties of P1, P2, and P3.

TABLE 3B

| Polymer | [Mon] M | Yield (%) | $\eta_{inh}$ | $T_g$ (° C.) (DSC) | $T_m$ (° C.) (DSC) | $T_{d,onset}$ (° C.) (TGA) |
|---|---|---|---|---|---|---|
| P2 | 0.061 | 75 | 0.417 | −58, −28 | None | 307 |
| P3 | 0.023 | 68 | 0.305 | −54, −18 | None | 337 |
| P1 | N/A | N/A | N/A | −57, 0 | 116 | 300 |

In Table 3B, inherent viscosity was measured in dichloroacetic acid at 25.0+/−0.1° C. DSC and TGA were performed at 10° C. per min and 20° C. per min, respectively, under nitrogen atmosphere.

The P2 and P3 microphase-separation is consistent with both polymers exhibiting two glass transition temperatures ($T_g$'s) in DSC measurements. As can be seen on Table 3B, P2 showed $T_g$'s at −58 and −28° C. while P3 had $T_g$'s at -54 and −18° C. The lower $T_g$'s correspond to the polyether-rich phase and the second $T_g$ to the peptide-rich domain. The higher $T_g$ of the polypeptide-rich phase observed for P3 is consistent with its longer polypeptide blocks while the lower $T_g$ of P2 reflects its higher segmental motion. The thermal data confirmed that PEG crystallization was completely suppressed as no $T_m$, was observed. The $T_m$ observed for P1 is results from peptide-rich domains.

The modulus and tensile strength of P2 and P3 were determined from stress-strain curves of their respective films and fibers. Table 4 summarizes the mechanical properties of the polymers. Each entry in Table 4 is an average of 3 to 5 measurements performed at a loading rate of 0.33-0.50% per s and all films were sheared at 30-60 cm·s$^{-1}$.

TABLE 4

Figure 1C:
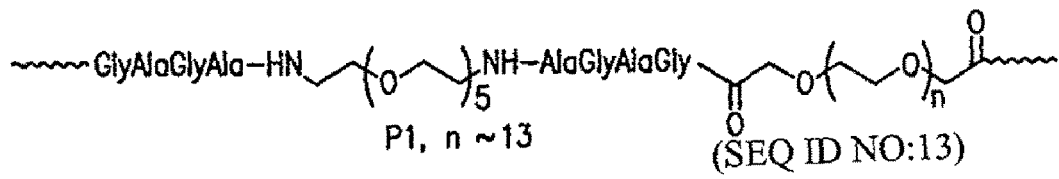
FIG. 1C shows the generic structure of yet another multiblock copolymer of the present invention, referred to herein as P1.
Figure 1D:
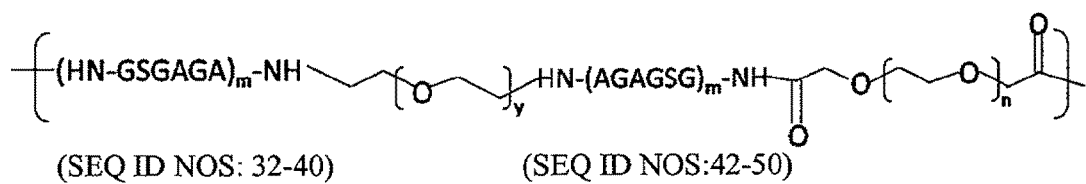
FIG. 1D shows the generic structure of another multiblock copolymer of the present invention.

| Polymer | Peptide Segment | Modulus (MPa) | Tensile Strength (MPa) | Elongation at Break (%) |
|---|---|---|---|---|
| P1 (Film) (from FIG. 1C) | (AlaGly)$_2$ SEQ ID NO: 51 | 210 +/− 9 | 14.0 +/− 0.4 | 21.2 +/− 6.0 |
| P2 (Film) | (Ala)$_4$ SEQ ID NO: 1 | 308 +/− 25 | 16.7 +/− 1.1 | 26.2 +/− 3.6 |
| P2 (Fiber) | (Ala)$_4$ SEQ ID NO: 1 | 410 +/− 35 | 13.0 +/− 1.4 | 22.9 +/− 13.6 |
| P3 (Film) | (Ala)$_6$ SEQ ID NO: 3 | 488 +/− 31 | 18.6 +/− 0.9 | 12.1 +/− 0.9 |
| P3 (Fiber) | (Ala)$_6$ SEQ ID NO: 3 | 750 +/− 156 | 14.2 +/− 2.7 | 5.4 +/− 1.7 |

As shown in Table 4, spider silk-inspired analogue P2, containing an average of 4 Ala residues per segment, shows higher modulus, tensile strength, and elongation at break than the *B. mori* silk-inspired P1, which also contains 4 peptide residues (AlaGlyAlaGly, SEQ ID NO. 41), results consistent with the fact that native spider silk has been shown to be stronger than native silkworm silk. Increasing the average poly(alanine) block length, as in P3, results in increased modulus and tensile strength. The elongation at break decreased significantly with increasing peptide sequence suggesting lower toughness for P3, which is a direct consequence of the increased stiffness of the hard segment.

The mechanical properties for P2 and P3 fibers, such as elongation and, hence, toughness of P2 are comparable to those of the natural silk fibers, while the modulus and tensile strength are within just an order of magnitude of those documented for regenerated *N. clavipes* silk and an artificial spider silk analogue protein.

It is to be understood that the above-described embodiments are simply illustrative of the principles of the invention. Various other modifications, changes, details and uses may be made by those skilled in the art that will embody the principles of the invention and fall within the spirit and scope thereof.

What is claimed is:

1. A composition, comprising the following formula:

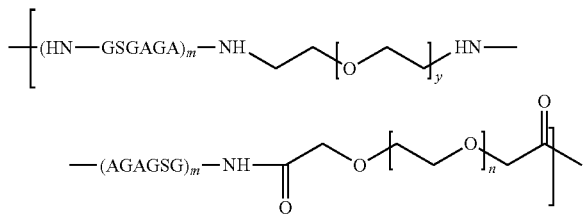

wherein n is an integer from 6 to 20, and wherein y is an integer from 1 to 5, and m is an integer from 1 to 9, and wherein $(GSGAGA)_m$, is SEQ ID NOs: 32-40 when m is 1-9, respectively and $(AGAGSG)_m$, is SEQ ID NOs: 42-50 when m is 1-9, respectively.

2. A multiblock copolymer, comprising the following structure:

-[peptide-linker$_1$-peptide]-1inker$_2$-[peptide-linker$_3$-peptide]-wherein the peptide blocks are selected from the group consisting of: $(GSGAGA)_m$, SEQ ID NOs: 32-40 when m is 1-9, respectively and $(AGAGSG)_m$, SEQ ID NOs: 42-50 when m is 1-9, respectively, wherein said linkers 1, 2, and 3 have the general formula $(A_xB)_n$ wherein A is either CRR' or SiRR', if A is CRR' then x is an integer from 1 to 4 and R and R' are independently chosen from H, methyl, ethyl, propyl, or if A is SiRR' then x is 1 and R and R' are independently chosen from methyl, ethyl, and vinyl; and B is a heteroatom selected from the group consisting of O, N, and S, wherein if B is N then the substituents on B are chosen from H, methyl, ethyl or propyl groups; and if A is $CH_2$ or $(CH_2)_2$ then n<20, if A is $(CH_2)_3$ or $(CH_2)_4$ then n is greater than or equal to 3.

* * * * *

UNITED STATES PATENT AND TRADEMARK OFFICE
CERTIFICATE OF CORRECTION

PATENT NO. : 7,989,586 B2  
APPLICATION NO. : 12/197646  
DATED : August 2, 2011  
INVENTOR(S) : Osman Rathore et al.

Page 1 of 1

It is certified that error appears in the above-identified patent and that said Letters Patent is hereby corrected as shown below:

In Column 28, line 31 (claim 2), "1inker" should read -- linker --

Signed and Sealed this
Twentieth Day of September, 2011

David J. Kappos
*Director of the United States Patent and Trademark Office*

SEQUENCE LISTING

<160> NUMBER OF SEQ ID NOS: 50

<210> SEQ ID NO 1

```
<211> LENGTH: 4
<212> TYPE: PRT
<213> ORGANISM: Nephila clavipes

<400> SEQUENCE: 1

Ala Ala Ala Ala
1

<210> SEQ ID NO 2
<211> LENGTH: 5
<212> TYPE: PRT
<213> ORGANISM: Nephila clavipes

<400> SEQUENCE: 2

Ala Ala Ala Ala Ala
1               5

<210> SEQ ID NO 3
<211> LENGTH: 6
<212> TYPE: PRT
<213> ORGANISM: Nephila clavipes

<400> SEQUENCE: 3

Ala Ala Ala Ala Ala Ala
1               5

<210> SEQ ID NO 4
<211> LENGTH: 7
<212> TYPE: PRT
<213> ORGANISM: Nephila clavipes

<400> SEQUENCE: 4

Ala Ala Ala Ala Ala Ala Ala
1               5

<210> SEQ ID NO 5
<211> LENGTH: 8
<212> TYPE: PRT
<213> ORGANISM: Nephila clavipes

<400> SEQUENCE: 5

Ala Ala Ala Ala Ala Ala Ala Ala
1               5

<210> SEQ ID NO 6
<211> LENGTH: 9
<212> TYPE: PRT
<213> ORGANISM: Nephila clavipes

<400> SEQUENCE: 6

Ala Ala Ala Ala Ala Ala Ala Ala Ala
1               5

<210> SEQ ID NO 7
<211> LENGTH: 10
<212> TYPE: PRT
<213> ORGANISM: Nephila clavipes

<400> SEQUENCE: 7

Ala Ala Ala Ala Ala Ala Ala Ala Ala Ala
1               5                   10

<210> SEQ ID NO 8
<211> LENGTH: 11
<212> TYPE: PRT
<213> ORGANISM: Nephila clavipes
```

```
<400> SEQUENCE: 8

Ala Ala Ala Ala Ala Ala Ala Ala Ala Ala
1               5                   10

<210> SEQ ID NO 9
<211> LENGTH: 12
<212> TYPE: PRT
<213> ORGANISM: Nephila clavipes

<400> SEQUENCE: 9

Ala Ala Ala Ala Ala Ala Ala Ala Ala Ala Ala Ala
1               5                   10

<210> SEQ ID NO 10
<211> LENGTH: 13
<212> TYPE: PRT
<213> ORGANISM: Nephila clavipes

<400> SEQUENCE: 10

Ala Ala Ala Ala Ala Ala Ala Ala Ala Ala Ala Ala Ala
1               5                   10

<210> SEQ ID NO 11
<211> LENGTH: 14
<212> TYPE: PRT
<213> ORGANISM: Nephila clavipes

<400> SEQUENCE: 11

Ala Ala Ala Ala Ala Ala Ala Ala Ala Ala Ala Ala Ala Ala
1               5                   10

<210> SEQ ID NO 12
<211> LENGTH: 15
<212> TYPE: PRT
<213> ORGANISM: Nephila clavipes

<400> SEQUENCE: 12

Ala Ala Ala Ala Ala Ala Ala Ala Ala Ala Ala Ala Ala Ala Ala
1               5                   10                  15

<210> SEQ ID NO 13
<211> LENGTH: 4
<212> TYPE: PRT
<213> ORGANISM: Bombyx mori

<400> SEQUENCE: 13

Gly Ala Gly Ala
1

<210> SEQ ID NO 14
<211> LENGTH: 8
<212> TYPE: PRT
<213> ORGANISM: Bombyx mori

<400> SEQUENCE: 14

Gly Ala Gly Ala Gly Ala Gly Ala
1               5

<210> SEQ ID NO 15
<211> LENGTH: 12
<212> TYPE: PRT
<213> ORGANISM: Bombyx mori

<400> SEQUENCE: 15
```

```
Gly Ala Gly Ala Gly Ala Gly Ala Gly Ala Gly Ala
1               5                   10
```

<210> SEQ ID NO 16
<211> LENGTH: 16
<212> TYPE: PRT
<213> ORGANISM: Bombyx mori

<400> SEQUENCE: 16

```
Gly Ala Gly Ala Gly Ala Gly Ala Gly Ala Gly Ala Gly Ala Gly Ala
1               5                   10                  15
```

<210> SEQ ID NO 17
<211> LENGTH: 20
<212> TYPE: PRT
<213> ORGANISM: Bombyx mori

<400> SEQUENCE: 17

```
Gly Ala Gly Ala Gly Ala Gly Ala Gly Ala Gly Ala Gly Ala Gly Ala
1               5                   10                  15

Gly Ala Gly Ala
            20
```

<210> SEQ ID NO 18
<211> LENGTH: 24
<212> TYPE: PRT
<213> ORGANISM: Bombyx mori

<400> SEQUENCE: 18

```
Gly Ala Gly Ala Gly Ala Gly Ala Gly Ala Gly Ala Gly Ala Gly Ala
1               5                   10                  15

Gly Ala Gly Ala Gly Ala Gly Ala
            20
```

<210> SEQ ID NO 19
<211> LENGTH: 28
<212> TYPE: PRT
<213> ORGANISM: Bombyx mori

<400> SEQUENCE: 19

```
Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala
            20              25
```

<210> SEQ ID NO 20
<211> LENGTH: 32
<212> TYPE: PRT
<213> ORGANISM: Bombyx mori

<400> SEQUENCE: 20

```
Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20              25                  30
```

<210> SEQ ID NO 21
<211> LENGTH: 36
<212> TYPE: PRT
<213> ORGANISM: Bombyx mori

<400> SEQUENCE: 21

```
Gly Ala Gly Ala Gly Ala Gly Ala Gly Ala Gly Ala Gly Ala Gly Ala
1               5                   10                  15
```

Gly Ala Gly Ala Gly Ala Gly Ala Gly Ala Gly Ala Gly Ala
            20                  25                  30

Gly Ala Gly Ala
        35

<210> SEQ ID NO 22
<211> LENGTH: 6
<212> TYPE: PRT
<213> ORGANISM: Bombyx mori

<400> SEQUENCE: 22

Gly Ala Gly Ala Gly Ser
1               5

<210> SEQ ID NO 23
<211> LENGTH: 12
<212> TYPE: PRT
<213> ORGANISM: Bombyx mori

<400> SEQUENCE: 23

Gly Ala Gly Ala Gly Ser Gly Ala Gly Ala Gly Ser
1               5                   10

<210> SEQ ID NO 24
<211> LENGTH: 18
<212> TYPE: PRT
<213> ORGANISM: Bombyx mori

<400> SEQUENCE: 24

Gly Ala Gly Ala Gly Ser Gly Ala Gly Ala Gly Ser Gly Ala Gly Ala
1               5                   10                  15

Gly Ser

<210> SEQ ID NO 25
<211> LENGTH: 24
<212> TYPE: PRT
<213> ORGANISM: Bombyx mori

<400> SEQUENCE: 25

Gly Ala Gly Ala Gly Ser Gly Ala Gly Ala Gly Ser Gly Ala Gly Ala
1               5                   10                  15

Gly Ser Gly Ala Gly Ala Gly Ser
            20

<210> SEQ ID NO 26
<211> LENGTH: 30
<212> TYPE: PRT
<213> ORGANISM: Bombyx mori

<400> SEQUENCE: 26

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser
            20                  25                  30

<210> SEQ ID NO 27
<211> LENGTH: 36
<212> TYPE: PRT
<213> ORGANISM: Bombyx mori

<400> SEQUENCE: 27

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala
        20                  25                  30

Gly Ala Gly Ser
        35

<210> SEQ ID NO 28
<211> LENGTH: 42
<212> TYPE: PRT
<213> ORGANISM: Bombyx mori

<400> SEQUENCE: 28

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
        20                  25                  30

Gly Ala Gly Ser Gly Ala Gly Ala Gly Ser
        35                  40

<210> SEQ ID NO 29
<211> LENGTH: 48
<212> TYPE: PRT
<213> ORGANISM: Bombyx mori

<400> SEQUENCE: 29

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
        20                  25                  30

Gly Ala Gly Ser Gly Ala Gly Ala Gly Ser Gly Ala Gly Ala Gly Ser
        35                  40                  45

<210> SEQ ID NO 30
<211> LENGTH: 54
<212> TYPE: PRT
<213> ORGANISM: Bombyx mori

<400> SEQUENCE: 30

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
        20                  25                  30

Gly Ala Gly Ser Gly Ala Gly Ala Gly Ser Gly Ala Gly Ala Gly Ser
        35                  40                  45

Gly Ala Gly Ala Gly Ser
        50

<210> SEQ ID NO 31
<211> LENGTH: 4
<212> TYPE: PRT
<213> ORGANISM: Bombyx mori

<400> SEQUENCE: 31

Gly Ala Gly Ala
1

<210> SEQ ID NO 32
<211> LENGTH: 6
<212> TYPE: PRT
<213> ORGANISM: Bombyx mori

<400> SEQUENCE: 32

-continued

Gly Ser Gly Ala Gly Ala
1               5

<210> SEQ ID NO 33
<211> LENGTH: 12
<212> TYPE: PRT
<213> ORGANISM: Bombyx mori

<400> SEQUENCE: 33

Gly Ser Gly Ala Gly Ala Gly Ser Gly Ala Gly Ala
1               5                   10

<210> SEQ ID NO 34
<211> LENGTH: 18
<212> TYPE: PRT
<213> ORGANISM: Bombyx mori

<400> SEQUENCE: 34

Gly Ser Gly Ala Gly Ala Gly Ser Gly Ala Gly Ala Gly Ser Gly Ala
1               5                   10                  15

Gly Ala

<210> SEQ ID NO 35
<211> LENGTH: 24
<212> TYPE: PRT
<213> ORGANISM: Bombyx mori

<400> SEQUENCE: 35

Gly Ser Gly Ala Gly Ala Gly Ser Gly Ala Gly Ala Gly Ser Gly Ala
1               5                   10                  15

Gly Ala Gly Ser Gly Ala Gly Ala
            20

<210> SEQ ID NO 36
<211> LENGTH: 30
<212> TYPE: PRT
<213> ORGANISM: Bombyx mori

<400> SEQUENCE: 36

Gly Ser Gly Ala Gly Ala Gly Ser Gly Ala Gly Ala Gly Ser Gly Ala
1               5                   10                  15

Gly Ala Gly Ser Gly Ala Gly Ala Gly Ser Gly Ala Gly Ala
            20                  25                  30

<210> SEQ ID NO 37
<211> LENGTH: 36
<212> TYPE: PRT
<213> ORGANISM: Bombyx mori

<400> SEQUENCE: 37

Gly Ser Gly Ala Gly Ala Gly Ser Gly Ala Gly Ala Gly Ser Gly Ala
1               5                   10                  15

Gly Ala Gly Ser Gly Ala Gly Ala Gly Ser Gly Ala Gly Ala Gly Ser
            20                  25                  30

Gly Ala Gly Ala
        35

<210> SEQ ID NO 38
<211> LENGTH: 42
<212> TYPE: PRT
<213> ORGANISM: Bombyx mori

<400> SEQUENCE: 38

```
Gly Ser Gly Ala Gly Ala Gly Ser Gly Ala Gly Ala Gly Ser Gly Ala
1               5                   10                  15

Gly Ala Gly Ser Gly Ala Gly Ala Gly Ser Gly Ala Gly Ala Gly Ser
                20                  25                  30

Gly Ala Gly Ala Gly Ser Gly Ala Gly Ala
            35                  40

<210> SEQ ID NO 39
<211> LENGTH: 48
<212> TYPE: PRT
<213> ORGANISM: Bombyx mori

<400> SEQUENCE: 39

Gly Ser Gly Ala Gly Ala Gly Ser Gly Ala Gly Ala Gly Ser Gly Ala
1               5                   10                  15

Gly Ala Gly Ser Gly Ala Gly Ala Gly Ser Gly Ala Gly Ala Gly Ser
                20                  25                  30

Gly Ala Gly Ala Gly Ser Gly Ala Gly Ala Gly Ser Gly Ala Gly Ala
            35                  40                  45

<210> SEQ ID NO 40
<211> LENGTH: 54
<212> TYPE: PRT
<213> ORGANISM: Bombyx mori

<400> SEQUENCE: 40

Gly Ser Gly Ala Gly Ala Gly Ser Gly Ala Gly Ala Gly Ser Gly Ala
1               5                   10                  15

Gly Ala Gly Ser Gly Ala Gly Ala Gly Ser Gly Ala Gly Ala Gly Ser
                20                  25                  30

Gly Ala Gly Ala Gly Ser Gly Ala Gly Ala Gly Ser Gly Ala Gly Ala
            35                  40                  45

Gly Ser Gly Ala Gly Ala
        50

<210> SEQ ID NO 41
<211> LENGTH: 4
<212> TYPE: PRT
<213> ORGANISM: Bombyx mori

<400> SEQUENCE: 41

Ala Gly Ala Gly
1

<210> SEQ ID NO 42
<211> LENGTH: 6
<212> TYPE: PRT
<213> ORGANISM: Bombyx mori

<400> SEQUENCE: 42

Ala Gly Ala Gly Ser Gly
1               5

<210> SEQ ID NO 43
<211> LENGTH: 12
<212> TYPE: PRT
<213> ORGANISM: Bombyx mori

<400> SEQUENCE: 43

Ala Gly Ala Gly Ser Gly Ala Gly Ala Gly Ser Gly
1               5                   10
```

```
<210> SEQ ID NO 44
<211> LENGTH: 18
<212> TYPE: PRT
<213> ORGANISM: Bombyx mori

<400> SEQUENCE: 44

Ala Gly Ala Gly Ser Gly Ala Gly Ala Gly Ser Gly Ala Gly Ala Gly
1               5                   10                  15

Ser Gly

<210> SEQ ID NO 45
<211> LENGTH: 24
<212> TYPE: PRT
<213> ORGANISM: Bombyx mori

<400> SEQUENCE: 45

Ala Gly Ala Gly Ser Gly Ala Gly Ala Gly Ser Gly Ala Gly Ala Gly
1               5                   10                  15

Ser Gly Ala Gly Ala Gly Ser Gly
            20

<210> SEQ ID NO 46
<211> LENGTH: 30
<212> TYPE: PRT
<213> ORGANISM: Bombyx mori

<400> SEQUENCE: 46

Ala Gly Ala Gly Ser Gly Ala Gly Ala Gly Ser Gly Ala Gly Ala Gly
1               5                   10                  15

Ser Gly Ala Gly Ala Gly Ser Gly Ala Gly Ala Gly Ser Gly
            20                  25                  30

<210> SEQ ID NO 47
<211> LENGTH: 36
<212> TYPE: PRT
<213> ORGANISM: Bombyx mori

<400> SEQUENCE: 47

Ala Gly Ala Gly Ser Gly Ala Gly Ala Gly Ser Gly Ala Gly Ala Gly
1               5                   10                  15

Ser Gly Ala Gly Ala Gly Ser Gly Ala Gly Ala Gly Ser Gly Ala Gly
            20                  25                  30

Ala Gly Ser Gly
        35

<210> SEQ ID NO 48
<211> LENGTH: 42
<212> TYPE: PRT
<213> ORGANISM: Bombyx mori

<400> SEQUENCE: 48

Ala Gly Ala Gly Ser Gly Ala Gly Ala Gly Ser Gly Ala Gly Ala Gly
1               5                   10                  15

Ser Gly Ala Gly Ala Gly Ser Gly Ala Gly Ala Gly Ser Gly Ala Gly
            20                  25                  30

Ala Gly Ser Gly Ala Gly Ala Gly Ser Gly
        35                  40

<210> SEQ ID NO 49
<211> LENGTH: 48
<212> TYPE: PRT
<213> ORGANISM: Bombyx mori
```

```
<400> SEQUENCE: 49

Ala Gly Ala Gly Ser Gly Ala Gly Ala Gly Ser Gly Ala Gly Ala Gly
1               5                   10                  15

Ser Gly Ala Gly Ala Gly Ser Gly Ala Gly Ala Gly Ser Gly Ala Gly
                20                  25                  30

Ala Gly Ser Gly Ala Gly Ala Gly Ser Gly Ala Gly Ala Gly Ser Gly
            35                  40                  45

<210> SEQ ID NO 50
<211> LENGTH: 54
<212> TYPE: PRT
<213> ORGANISM: Bombyx mori

<400> SEQUENCE: 50

Ala Gly Ala Gly Ser Gly Ala Gly Ala Gly Ser Gly Ala Gly Ala Gly
1               5                   10                  15

Ser Gly Ala Gly Ala Gly Ser Gly Ala Gly Ala Gly Ser Gly Ala Gly
                20                  25                  30

Ala Gly Ser Gly Ala Gly Ala Gly Ser Gly Ala Gly Ala Gly Ser Gly
            35                  40                  45

Ala Gly Ala Gly Ser Gly
    50
```